United States Patent [19]

Paulson et al.

[11] Patent Number: 5,032,519
[45] Date of Patent: Jul. 16, 1991

[54] METHOD FOR PRODUCING SECRETABLE GLYCOSYLTRANSFERASES AND OTHER GOLGI PROCESSING ENZYMES

[75] Inventors: James C. Paulson, Sherman Oaks; Eryn Ujita-Lee, Redondo Beach; Karen J. Colley, Los Angeles; Beverly Adler, Newbury Park; Jeffrey K. Browne, Camarillo, all of Calif.

[73] Assignee: The Regents of the Univ. of California, Oakland, Calif.

[21] Appl. No.: 426,577

[22] Filed: Oct. 24, 1989

[51] Int. Cl.$^5$ .................... C12N 15/00; C12N 15/54; C12N 15/63; C12N 15/79

[52] U.S. Cl. .................... 435/193; 435/320.1; 435/112.3; 435/240.2; 935/48; 935/60; 935/70

[58] Field of Search ............ 435/69.1, 320, 240.2, 435/172.3, 193; 536/27

[56] References Cited

PUBLICATIONS

Gil et al, Cell, vol. 41, 249–258 (1985).
Colley, K. J., Lee, E. U., Adler, B., Browne, J. K., and Paulson, J. C. (1989), Conversion of a Golgi Apparatus Sialyltransferase to a Secretory Protein by Replacement of the NH$_2$-Terminal Signal Anchor with a Signal Peptide, J. Biol. Chem. 264, 17619–17622.
Joziasse, D. H., Shaper, J. H., Van den Eijnden, D. H., Van Tunen, A. J., and Shaper, N. L. (1989), Bovine α1→3-Galactosyltransferase: Isolation & Char. of a cDNA Clone, J. Biol. Chem. 264, 14290–14297.
Kukowska-Latallo, J., Larsen, R. D., Nair, R. P., and Lowe, J. B. (1990), A Cloned Human cDNA Det. Exp. of a Mouse Stage-Specific . . . Genes Dev. 4, 1288–1303.
Larsen, R. D., Rajan, V. P., Ruff, M. M., Kukowska-Latallo, J., Cummings, R. D., and Lowe, J. B. (1989), Isolation of a cDNA . . . Proc. Natl. Acad. Sci., U.S.A. 86, 8227–8231.
Larsen, R. D., Ernst, L. K., Nair, R. P. and Lowe, J. B. (1990), Molecular Cloning, Sequence, and Expression . . . Proc. Natl. Acad. Sci., U.S.A. 87, 6674–6678.
Nakazawa, K., Ando, T., Kimura, T., and Narimatsu, H. (1988), Cloning and Sequencing of a Full-Length cDNA . . . J. Biochem. (Tokyo), 104, 165–168.
Narimatsu, H., Sinha, S., Brew, K., Okayama, H. and Quasba, P. K. (1986), Cloning and Sequencing of cDNA of Bovine . . . Proc. Natl. Acad. Sci., U.S.A. 83, 4720–4724.
Paulson, J. C., Weinstein, J., Ujita, E. U., Riggs, K. J., and Lai, P.-H. (1987), The Membrane Binding Domain of a Rat Liver . . . Biochem. Soc. Trans. 15, 618–620.
Shaper, N. L., Shaper, J. H., Meuth, J. L., Fox, J. L., Chang, H., Kirsch, I. R., and Hollis, G. F. (1986), Bovine Galactosyltransferase . . . Proc. Natl. Acad. Sci., U.S.A. 83, 1573–1577.
Shaper, N. L., Hollis, G. F., Douglas, J. G., Kirsch, I. R. and Shaper, J. J. H. (1988), Characterization of the Full Length cDNA for Murine β1,4-Galactosyltransferase . . . J. Biol. Chem. 263, 10420–10428.
Weinstein, J., Lee, E. U., McEntee, K., Lai, P.-H. and Paulson, J. C. (1987), Primary Structure of β-Galactoside . . . J. Biol. Chem. 262, 17735–17743.

(List continued on next page.)

*Primary Examiner*—Richard A. Schwartz
*Assistant Examiner*—S. L. Nolan
*Attorney, Agent, or Firm*—Poms, Smith, Lande & Rose

[57] ABSTRACT

A method for genetically engineering cells to produce soluble and secretable Golgi processing enzymes instead of naturally occurring membrane-bound enzymes. Cells are genetically engineered to express glycosyltransferases which lack both a membrane anchor and a retention signal. The resulting altered enzyme becomes soluble and secretable by the cell without losing its catalytic activity. Secretion of the soluble glycosyltransferase by the cell provides for increased production and simplified recovery of glycosyltransferases.

23 Claims, 6 Drawing Sheets

OTHER PUBLICATIONS

Yamamoto, F., Marken, J., Tsuji, T., White, T., Clausen, H. and Hakomori, S. (1990), Cloning and Characterization of DNA Complementary . . . J. Biol. Chem. 265, 1146–1151.

Yamamoto, F., Clausen, H., White, T., Marken, J., and Hakomori, S. (1990), Molecular Genetic Basis of the . . . Nature 345, 229–233.

Paulson, J. C. and Colley, K. J. (1989), Glycosyltransferases–Structure, Localization and Control of Cell . . . Journal of Biol. Chem., vol. 264, No. 30, Oct. 25, pp. 17615–17618.

Tetrahdedron Reports, 1989, "Enzyme-Catalyzed Synthesis of Carbohydrates", Eric J. Toone et al.

Ann. Rev. Cell Biol., 1988, 4:257–88, "Regulation of Protein Export from the Endoplasmic Reticulum", John K. Rose and Robert W. Doms, pp. 257–288.

The Journal of Biological Chemistry, vol. 257, No. 22, Nov. 25 issue, pp. 13835–13844, 1982, "Purification of a Gal$\beta$1 4GlcNAc . . . to Homogeneity from Rat Liver", J. Weinstein, U. deSouza-e Silva, and J. C. Paulson.

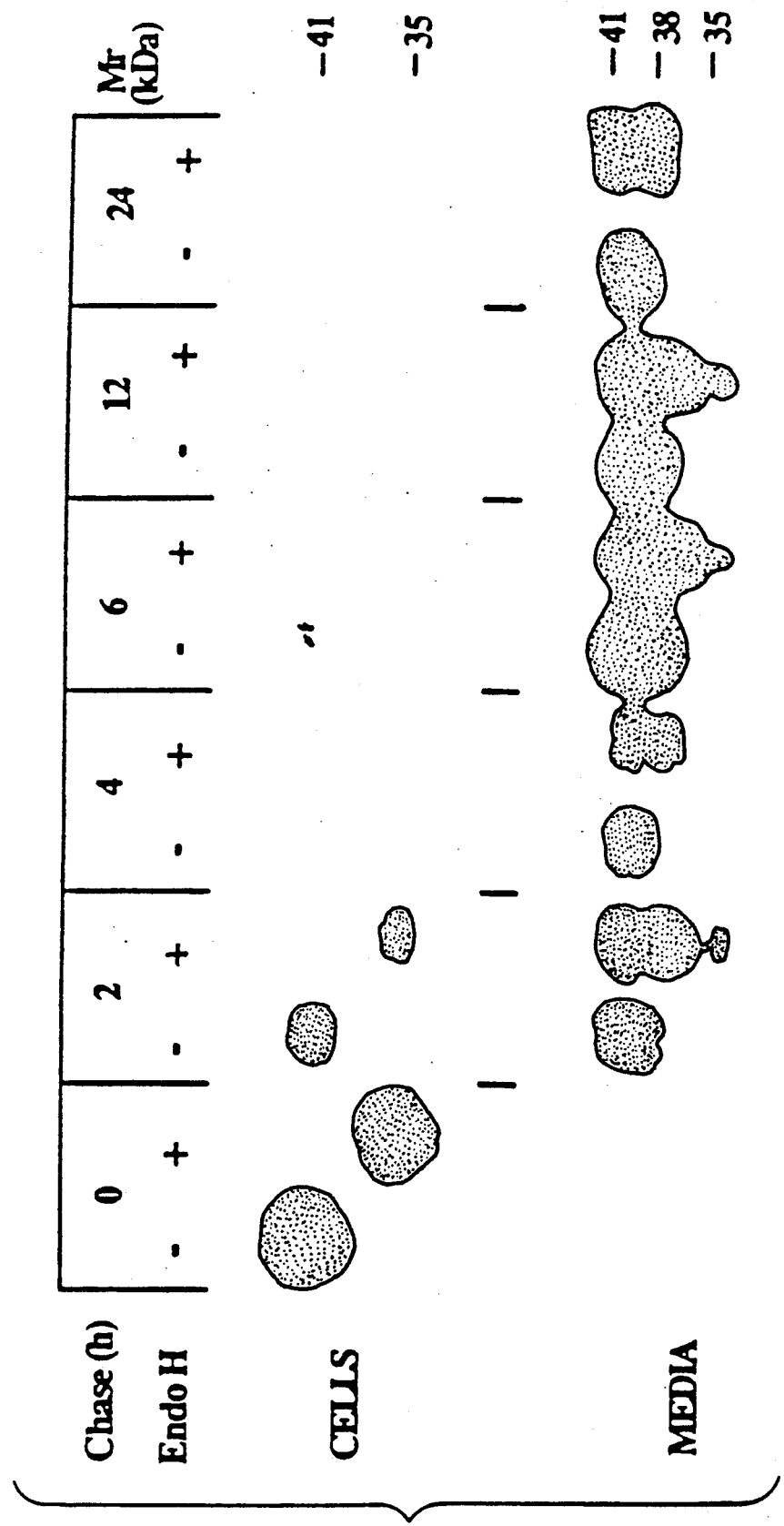

5,032,519

METHOD FOR PRODUCING SECRETABLE GLYCOSYLTRANSFERASES AND OTHER GOLGI PROCESSING ENZYMES

This invention was made with government support under Grant Contract Nos. GM-27904 and GM-11557 awarded by the National Institute of Health. The government has certain rights in this invention. The publications and other reference materials referred to herein to describe the background of the invention and to provide additional detail regarding its practice are hereby incorporated by reference. For convenience, the reference materials are numerically referenced and grouped in the appended bibliography.

BACKGROUND OF THE INVENTION

1. Field of the Invention

The present invention relates generally to the cellular mechanisms and enzymes involved in the glycosylation of proteins manufactured by the cell. More particularly, the present invention involves altering the enzyme production capabilities of a cell in order to produce a soluble glycosyltransferase which is secreted by the cell and recovered for further use.

2. Description of Related Art

Glycosyltransferases are important enzymes which are essential to the cellular sunthesis of carbohydrates. The glycosyltransferases and their role in enzyme-catalyzed synthesis of carbohydrates are presently being extensively studied (43,44). These enzymes exhibit high specificity for forming carbohydrate structures of defined sequence. Consequently, purified glycosyltransferases are increasingly used as enzymatic catalysts in carbohydrate synthesis. Application of these enzymes has been limited because of difficulties in isolating and purifying them. As a result, glycosyltransferases are only available in very small amounts and are extremely expensive.

The isolation and purification of glycosyltransferases is difficult because of their low abundance in cells and because the enzymes are membrane-bound glycoproteins which reside in the Golgi apparatus of cells. Accordingly, the present purification procedures involve the use of animal tissues from which the enzymes must be extracted and purified. These purification procedures are not amenable to large scale production and therefore are not well suited to meet the present and future demands for purified enzymes to be used in research and in industrial applications involving synthesis of carbohydrates.

As a result, there is presently a need to provide methods for producing increased amounts of purified glycosyltransferases wherein the method is amenable to relatively large scale production of purified enzymes.

SUMMARY OF THE INVENTION

In accordance with the present invention, a method is disclosed for producing catalytically active glycosyltransferases which are soluble and therefore readily secreted from cells. The secretion of relatively large quantities of such catalytically active enzymes provides a simplified procedure for purifying and recovering the glycosyltransferases. The invention is based upon the discovery that glycosyltransferases may be converted from membrane-bound proteins to soluble proteins without destroying their enzymatic character.

The present invention involves genetically altering a cell so that it produces a soluble glycosyltransferase instead of the normal membrane-bound glycosyltransferase. It was discovered that cells can be genetically altered to produce soluble glycosyltransferases which are readily secreted by the cell. The secreted glycosyltransferases are then readily recovered by conventional procedures for use in industrial applications and research involving carbohydrate synthesis.

As a feature of the present invention, it was discovered that the membrane domain and the stem portion of glycosyltransferases functioned, respectively, as the membrane anchor and retention signal to keep the enzyme bound to the Golgi membrane. Further, it was discovered that the enzymatic activity of glycosyltransferases is not dependent on the stem portion so that it can be removed or replaced without destroying the catalytic activity of the glycosyltransferase. In accordance with the present invention, genes are introduced into the cell which express glycosyltransferases that have the membrane anchor and stem portion replaced with a cleavable secretion-signal peptide. As a result, the glycosyltransferase becomes soluble and is secreted by the cell.

The above discussed and many other features and attendant advantages of the present invention will become better understood by reference to the following detailed description when taken in conjunction with the accompanying drawings.

BRIEF DESCRIPTION OF THE DRAWINGS

FIG. 5 shows test results demonstrating that the intracellular form of ST is sensitive to Endo H while the secreted ST is resistant to Endo H.

DETAILED DESCRIPTION OF THE INVENTION

Figure 1:
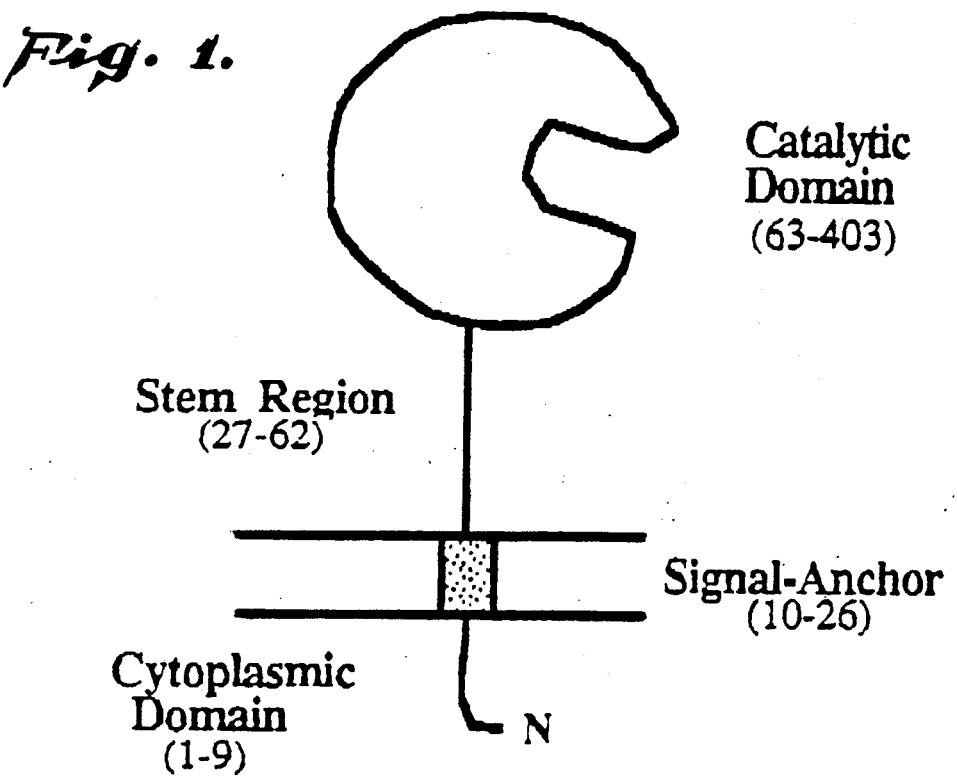
FIG. 1 shows the domain structure of the sialytransferase which is anchored to Golgi apparatus membranes by an $NH_2$-terminal hydrophobic domain. The stem region is believed to carry the retention signal that keeps the enzyme in the Golgi apparatus.

The present invention involves controlling the production of glycosyltransferases in a cell by using genetic engineering to instruct the cell to produce glycosyltransferases which are soluble and can be secreted by the cell. This is accomplished by instructing the cell to produce glycosyltransferases which are lacking both a membrane anchor domain and a retention signal which are believed to normally anchor the glycosyl-transferase in the Golgi apparatus of the cell. The cell is instructed to secrete the glycosyl-transferase, as opposed to producing it intracellularly, by incorporating in the genetic material the instructions for producing a cleavable secretion-signal peptide. It was discovered that the membrane anchor and retention signal can be removed from glycosyltransferases without destroying the catalytic activity of the enzyme. The resulting soluble peptide is sorted by the cell and transported out of the cell for recovery and further use.

A major consideration in cell biology is sorting and transport of glycosyltransferases and other membrane glycoproteins to their multiple destinations. One hypothesis is that glycoproteins destined for the cell surface are transported by a default pathway and require no routing information, while glycoproteins destined for other subcellular localizations require signals that assist in their sorting and transport (1-3). One well documented transport signal is the mannose 6-phosphate recognition marker found on some lysosomal enzymes (4). These transport signals mediate the enzymes' recognition by mannose 6-phosphate receptors which transport them to the lysosomes as they exit the biosynthetic pathway from the trans-Golgi. In the case of resident proteins of the ER and the Golgi apparatus, the putative signals are viewed as retention signals, since the transport mechanism is likely the same as the default pathway, and the proteins must then resist the flow of the default pathway once they arrive at their site of residence (1-3).

Progress has been made in elucidating the retention signals for the endoplasmic reticulum (ER) retained proteins (6-10). Analysis of deletion mutants and fusion proteins of soluble ER proteins such as protein disulfied isomerase, prolyl hydroxylase, grp78, and grp94 has demonstrated that a COOH-terminal Lys-Asp-Glu-Leu sequence is sufficient for retention in the ER (6,7). In this case a resident Lys-Asp-Glu-Leu receptor protein is postulated for retention of these proteins, although such a receptor has not been identified. Less is knwon about the retention signals of membrane-bound proteins of the ER (8-10).

Elucidation of the signals for retention of membrane proteins in the Golgi apparatus has been equally refractory. Machamer and Rose (11) have demonstrated that the first of three membrane-spanning regions of the E1 protein of coronavirus is required for the localization/retention of this viral protein to the cis- to medial-Golgi complex. How this region participates in Golgi apparatus localization is not yet understood.

$\beta$-galactoside $\alpha$2,6-sialytransferase is a membrane bound glycosyltransferase of the Golgi apparatus which participates in the addition of terminal sialic acid residues to N-linked oligosaccharide chains. Studies have been conducted to identify the structural basis for localization of this enzyme within the cell (14,15). In rat liver hepatocytes, hepatoma cells, and in intestinal globlet cells, $\beta$-galactoside $\alpha$2,6-sialytransferase has been localized by immunoelectron microscopy to the transcisternae of the Golgi and the trans-Golgi network, whereas in intestinal absorptive cells, the enzyme is more diffusely localized throughout the cisternal stacks (14-16).

As diagrammed in FIG. 1, the rat liver sialytransferase is believed to be a class II membrane glycoprotein protein with a 9-amino acid $NH_2$-terminal cytoplasmic tail, a 17-amino acid signal-anchor domain, and a luminal domain which includes an exposed stem region followed by a 41-kDa catalytic domain (19). The existence of an exposed stem region was initially suggested by the purification of a soluble form of the rat liver sialytransferase which was missing the first 62 amino acids due to proteolytic degradation during isolation. Soluble forms of the sialytransferase also are found in various secretions and body fluids including milk and colostrum (18) and serum (20,21). The slow release of the sialytransferase catalytic domain from the transmembrane anchor, through the action of endogenous proteases in the Golgi apparatus or trans-Golgi network, has been proposed to account for the appearance of the soluble enzyme in these fluids (21,22).

The above considerations suggest that sialytransferase may act like any other secretory protein once released from its $NH_2$-terminal signal-anchor, providing that the signal for retention in the Golgi apparatus is not part of the catalytic domain of the enzyme. As set forth in more detail below, the present invention is based on the discovery that the $NH_2$-terminal signal-anchor and stem region of the sialytransferase can be replaced with a cleavable signal sequence to produce a secretable enzyme which retains its catalytic activity.

In accordance with the present invention, it was found that removal of the sialytransferase membrane-anchor alone is not sufficient for rapid and efficient secretion of the soluble glycosyltransferase. Construction and expression of a sialytransferase mutant in which the anchor sequence is replaced by a cleavable signal peptide by recombinant DNA techniques results in a soluble sialytransferase missing the membrane-anchor but containing the intact stem region. This mutant is localized to the Golgi apparatus prior to being slowly secreted from the cell ($t_\frac{1}{2} \geq 24$ hours). In contrast, the soluble sialytransferase construct missing the stem region is rapidly secreted from the cell ($t_\frac{1}{2} = 2-3$ hours). These results show that a retention signal for Golgi apparatus localization resides in the stem region of the sialytransferase and, in accordance with the present invention, the stem region as well as the signal-anchor domain of the sialytransferase must be removed for rapid and efficient secretion of the soluble glycosyltransferase.

The present invention basically involves transfecting a host cell with a vector carrying a gene which expresses a glycosyltransferase that has the membrane anchor and most of the stem region replaced with a cleavable secretion signal segment. The resulting soluble glycosyltransferase, when expressed in the cell, is secreted by the cell. The secreted soluble glycosyltransferase is then separated from the cell media for use in industrial applications or carbohydrate synthesis research. Accordingly, the invention provides a useful procedure for producing relatively large amounts of easily recoverable glycosyltransferases which retain their catalytic activity.

The invention has wide application to the production of glycosyltransferases including N-acetylglucosaminaltransferases, N-acetylgalactosaminyltransferases, sialyl-transferases, fucosyltransferases, galacosyltransferases and mannosyltransferases providing that they exhibit similar topology to the sialytransferase. Indeed, as summarized in FIG. 2 and Table I, other glycosyltransferase cDNAs cloned to date also exhibit an $NH_2$-terminal signal-anchor sequence like the sialytransferase, predicting the same topology found for the sialytransferase (FIG. 1). Other classes of Golgi apparatus enzymes involved in post-translational modifications may also exhibit similar topology, such as sulfotransferases, glycosidases, acetyltransferases, mannosidases, and could also be produced by this method. The following description will be limited to the production of a soluble sialyltransferase with it being recognized by those skilled in the art that other glycosyltransferases and Golgi processing enzymes having similar membrane attachment structures can also be produced in secretable forms in accordance with the present invention.

TABLE 1

| Glycosyltransferase | Donor Substrate | Sequence Formed |
|---|---|---|
| Galactosyltransferases | | |
| GlcNAc$\beta$1,4-GT (E.C. 2.4.1.38) | UDP-Gal | Gal$\beta$1,4GlcNAc-R |
| Gal$\alpha$1,3-GT (E.C. 2.4.1.151) | UDP-Gal | Gal$\alpha$1,3Gal$\beta$1,4GlcNAc-R |
| Sialyltransferase | | |
| Gal$\alpha$2,6-ST (E.C. 2.4.99.1) | CMP-NeuAc | NeuAc$\alpha$2,6Gal$\beta$1,4GlcNAc-R |
| Fucosyltransferases | | |
| GlcNAc$\alpha$1,3-FT (E.C. 2.4.1.65) | GDP-Fuc | Fuc$\alpha$1,3 GlcNAc-R Gal$\beta$1,4 Fuc$\alpha$1,4 GlcNAc-R Gal$\beta$1,3 |
| Gal$\alpha$1,2-FT (E.C. 2.4.1.69) | GDP-Fuc | Fuc$\alpha$1,2Gal$\beta$1,4GlcNAc-R Fuc$\alpha$1,2Gal$\beta$1,3GalNAc-R |
| N-Acetylgalactosaminyltransferase | | |
| Gal$\alpha$1,3-GalNAcT (Blood group A transferase) | UDP-GalNAc | GalNAc$\alpha$1,3 Gal-R Fuc$\alpha$1,2 |

The host cell which is transfected can be any of the well known cell lines which are capable of producing glycosyltransferases. Exemplary cell lines include Chinese hamster ovary (CHO) cells, mouse L cells, mouse A9 cells, baby hamster kidney cells, C127 cells, PC8 cells, insect cells yeast (saccharomyces cerevisae) and other eukaryotic cell lines capable of the expression of glycosyltransferases. The particular procedure used to introduce the altered genetic material into the host cell for expression of the soluble glycosyltransferse is not particularly critical. Any of the well known procedures for introducing foreign nucleotide sequences into host cells may be used. These include the use of plasma vectors, viral vectors and any of the other well known methods for introducing cloned genomic DNA, cDNA, synthetic DNA or other foreign genetic material into a host cell. It is only necessary that the particular genetic engineering procedure utilized be capable of successfully introducing at least one gene into the host cell which is capable of expressing the altered glycosyltransferases.

The particular vector used to transport the genetic information into the cell is also not particularly critical. Any of the conventional vectors used for expression of recombinant glycoproteins in eukaryotic cells may be used. Exemplary vectors include pMSG, pAV009/A+, pMTO10/A+, pMAMneo-5, bacculovirus, pDSVE, and any other vector allowing expression of glycoproteins under the direction of the SV-40 early promoter, SV-40 late promoter, metallothionein promoter, murine mammary tumor virus promoter, Rous sarcoma virus promoter, polyhedrin promoter, or other promoters shown effective for expression in eukaryotic cells. For high expression of glycosyltransferases it is desirable to use a vector containing a DHFR gene such as pAV00-9/A+, pMT010/A+ or the exemplary vector pDSVE described in detail below. Such vectors used in combination with CHO cells which are lacking DHFR (e.g., CHO DHFR) allow amplification of the vector DNA carrying the glycosyltransferase gene by selection of the cells with methotrexate. However, other selectable markers resulting in gene amplification such as the sodium, potassium ATPase gene and ouabain selection (45) would be equally suitable. Alternatively, high yield expression systems not involving gene amplification would also be suitable, such as using a bacculovirus vector in insect cells, with the glycosyltransferase under the direction of the polyhedrin promoter (46).

The following example of the present invention is limited to the transfection of CHO cells with a gene capable of expressing $\beta$-galactoside $\alpha$2,6-sialyltransferase (ST) in a modified form wherein the membrane anchor and retention signal located at the NH$_2$ terminal region of the sialyltransferase are replaced with the cleavable signal peptide of human gamma-interferon. The cleavable signal sequence is required for targeting the modified glycosyltransferase to the secretory machinery of the cell (endoplasmic reticulum, Golgi apparatus, etc.), but the choice of the cleavable sequence is also not particularly critical. Other cleavable sequences could be used such as the insulin signal sequence (47), the tissue plasminogen activator signal sequence (used in the commercial vector pMAMneo-S) or any other cleavable signal sequence. Thus it will be understood that the principles disclosed with respect to the expression and secretion of soluble sialyltransferase (sp-ST) by CHO cells also applies to the other various glycosyltransferses, host cells, vectors and cleavable signal sequences previously mentioned.

The following example demonstrates the production and recovery of a secretable sialyltransferase which is compared to membrane-bound sialyltransferase. The example is as follows:

MATERIALS

The pECE expression vector used to express the membrane-bound sialyltransferase was obtained from Dr. William J. Rutter (University of California at San Francisco School of Medicine—Department of Biochemistry and Biophysics) (23), and CHO cells were obtained from Dr. L. Shapiro (University of California at Los Angeles School of Medicine). Tran $^{35}$S-label (85% methionine and 15% cysteine) (>1000 Ci/mmol) was purchased from ICN Biomedicals, Inc. (Irvine, Calif.), and γ-$^{32}$P-ATP(1000 μCi/ml) was obtained from New England Nuclear (Boston, Mass.). Restriction enzymes used in fusion protein construction were obtained from Bethesda Research Laboratories (Indianapolis, Ind.) and International Biotechnology Incorporated (New Haven, Conn.)). All cell culture reagents were obtained from IBCO (Grand Island, N.Y.). Endo-β-N-acetylglucosaminidase H (Endo H) in 10 mmol/1 phosphate buffer was purchased from Boehringer Mannheim Biochemicals (Indianapolis, Ind.). Immunoprecipitin was obtained from Bethesda Research Laboratories (Gaithersburg, Md.) and prepared according to the manufacturer's directions. Dimethyl sulfoxide was purchased from Sigma (St. Louis, Mo.) and 2,5 diphenyl oxazole was obtained from Aldrich (Milwaukee, Wis.). Methotrexate was purchased from Sigma (St. Louis, Mo.). The expression vector used for expressing the soluble sialyltransferase was pDSVE (described in U.S. Patent Application Ser. Nos. 025,344 and 152,045, the contents of which are hereby incorporated by reference).

CONSTRUCTION OF THE SIGNAL PEPTIDE-SIALYLTRANSFERASE (SP-ST) FUSION PROTEIN

To generate a secreted sialyltransferase, the 5′169 nucleotides (through amino acid 57) of the sialytransferase coding sequence in the ST3 cDNA were replaced with a synthetic gene segment coding for the 23 amino acid signal peptide and first three amino acids of human gamma interferon yielding the fusion gene product shown in FIG. 1. The sialyltransferase coding sequence in the ST3 cDNA was first modified by the introduction of a unique BamH1 site at nucleotides 163–171 (amino acids 55–57) and a unique Sall site in the 3′ untranslated region at nucleotides 1395–1400 by site-directed mutagenesis (24). The modified BamH1-Sall sialyltransferase gene fragment was isolated and ligated through the BamH1 site, with the synthetic gamma interferon signal peptide gene fragment and inserted into the pDSVE eukaryotic expression vector. Expression of the sialyltransferase gene is driven by the SV40 early gene promoter and uses the SV40 early gene polyadenylation signal. In addition, the vector contains a mouse dihydrofolate reductase (DHFR) gene as a selectable marker (25).

EXPRESSION OF THE MEMBRANE-BOUND AND SOLUBLE SIALYLTRANSFERASES IN CHO CELLS

The membrane-bound α2,6 sialyltransferase was expressed via the transfection of CHO DHFR cells with the pECE vector. Isolation of a stably transfected CHO cell clone expressing the membrane-bound α2,6 sialyltransferase from the SV40 early promoter of the pECE vector has been described by Lee et al. (26). The secreted sialyltransferase expression vector was introduced into a CHO DHFR cell line by the calcium phosphate microprecipitation method (27), modified as described (28,29). Following selection by growth in media with dialyzed serum pools of stably transfected CHO cells were obtained, and were further selected with methotraxate stepwise to 0.3 μM.

PULSE-CHASE ANALYSIS AND IMMUNOPRECIPITATION OF SIALYLTRANSFERASE PROTEINS

CHO cells stably expressing either the wild type sialyltransferase or the sp-ST fusion protein were grown on 100 mm plastic dishes until confluent and then incubated with methionine-free D-MEM for one hour. Media was removed, cells were washed and 2.5 ml methionine-free D-MEM with 100 mCi/ml Trans $^{35}$S-label was added to each dish. After one hour the media was removed, cells were washed with phosphate buffered saline (PBS) and then incubated for various times up to 24 hours with α-MEM, 5% fetal bovine serum (chase period). Following the chase period, media was collected, cells washed in PBS and lysed with 2.5 ml of immunoprecipitation buffer (50 mM Tris-HCl, pH 7.5, 150 mM NaCl, 5 mM EDTA, 0.5% Nonidet P-40, 0.1% SDS).

Sialyltransferase protein was immunoprecipitated from media and cell lysates at each time point. Eight μl of preimmune rabbit serum was incubated with 500 μl of sample for 15 minutes at 25° C. Eighty microliters of a 10% suspension of S. aureus in immunoprecipitation buffer was added to each tube, and incubation was continued for an additional 15 minutes. S. aureus-immune complexes were pelleted by centrifugation at 16,000×g for 1 minute. Supernatants were transferred to a new tube and incubated with 8 μl affinity purified rabbit anti-rat α2,6 sialyltransferase antibody for approximately 16 hours at 4° C. Again, 80 μl of a 10% suspension of S. aureus was added to each tube and incubation was continued for 30 minutes at 25° C. Samples were always subjected to end-over-end rotation during all of the previously described incubations. S. aureus-immune complexes were pelleted as described above and pellets washed three times with immunoprecipitation buffer and once with 10 mM Tris-HCl, pH 7.5, 0.1% SDS. Sialyltransferase protein was eluted from S. aureus pellets by boiling 5 minutes in 40 μl 1× Laemmli gel sample buffer (10% glycerol, 2% SDS, 65 mM Tris-HCl, pH 7.5, 0.5 mg/ml bromphenol blue, 10% β-mercaptoethanol). Immunoprecipitated proteins were electrophorsed on 10% polyacrylamide gels according to the method of Laemmli (30). Radiolabeled proteins were visualized by fluorography using 2,5 diphenyloxazole/-dimethyl sulfoxide (31) and gels were exposed to Kodak XAR-5 film at −80° C.

ENDO-β-N-ACETYLGLUCOSAMINIDASE H DIGESTIONS

After the final wash of the S. aureus pellets, immunoprecipitated proteins were treated essentially as described in Dahms et al. (32). Following acetone precipitation, protein pellets were resuspended in 20 μl Endo H buffer (0.1M sodium citrate, pH 6.0, 0.075% SDS, 0.2% β-mercaptoethanol), 2 mU Endo H was added and the digests were incubated at 37° C. for 16 hours. To stop the digestions, 20 μl of a 2x gel sample buffer was added to each tube and then samples were boiled for 5 minutes in preparation for SDS-polyacrylamide gel electrophoresis.

CDP-HEXANOLAMINE-AGAROSE AFFINITY CHROMATOGRAPHY

Affinity chromatography of unlabeled and radiolabeled CHO cell media was performed on small columns (1.5 ml) of CDP-hexanolamine-agarose essentially as described by Weinstein et al. (33). Columns were equilibrated with Buffer E (10 mM Na cacodylate, pH 6.5, 0.1% Triton CF-54, 0.15M NaCl) and after application of media (1.25 ml diluted iwth 1.25 ml of Buffer E) columns were developed by application of 1.2 ml Buffer E, 4.2 ml Buffer H (25 mM Na cacodylate, pH 5.3, 0.1% Triton CF-54, 0.15M NaCl) and 3 ml Buffer H plus 1 mM CDP (Elute, 1 mM CDP). Fractions of 300 μl were collected and assayed for total protein using the Pierce BCA protein detection assay and for sialyltransferase either by direct enzyme activity or by immunoprecipitation of $^{35}$S-labeled sialyltransferase protein followed by SDS polyacrylamide gel electrophoresis.

SIALYLTRANSFERASE ASSAY

Sialyltransferase assays were performed essentially as described previously (33) using CMP-[$^{14}$C] NeuAc (285,000 cpm/nmole) as a donor substrate and asialo $\alpha_1$ acid glycoprotein (50 μg) as the acceptor substrate. Observed activity in the elution fractions was corrected for the inhibition produced by the presence of CDP in the assay. Activity is reported as cpm transferred/10 μl/hr.

Figure 3:
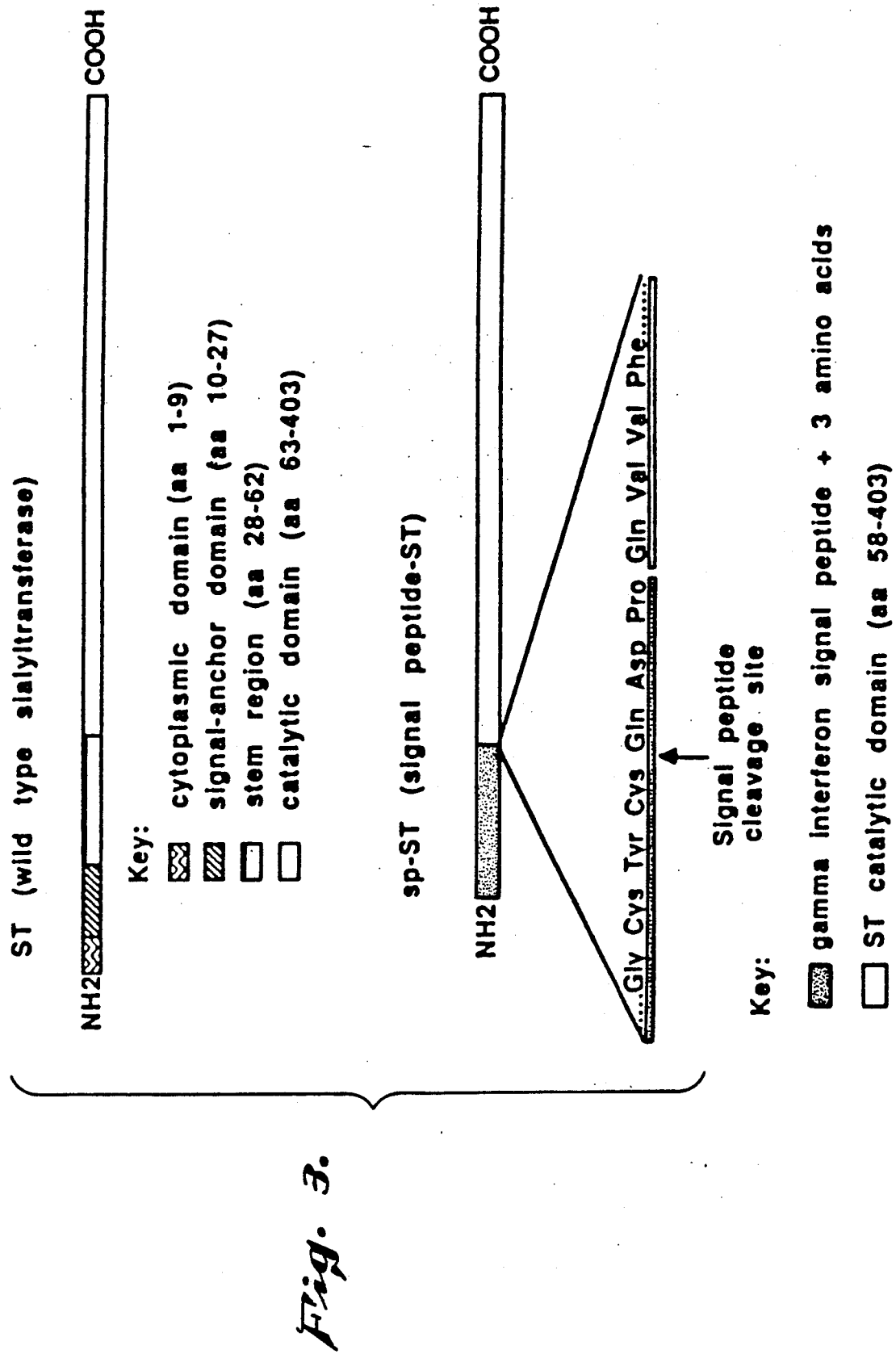
FIG. 3 shows an exemplary construction of a soluble sialyltransferase (sp-ST) in accordance with the present invention as compared to the construction of a membrane bound sialyltransferase (ST).

In FIG. 3, the structure of the ST (wild type) sialyltransferase is compared to the fusion sialyltransferase (sp-ST). The fusion protein or signal peptide-sialyltransferase (sp-ST), consists of residues 1-26 of human gamma interferon including the cleavable signal peptide (34), and amino acids 58-403 of the sialyltransferase. The NH$_2$-terminal cytoplasmic tail, signal-anchor domain and most of the putative stem region of the wild type sialyltransferase are missing, however, the sp-ST enters the secretory pathway using the gamma interferon signal peptide. CHO cells were transfected with either the wild type sialyltransferase cDNA (26) or the sp-ST cDNA and stably expressing CHO cell clones were isolated as described above.

Figure 4:
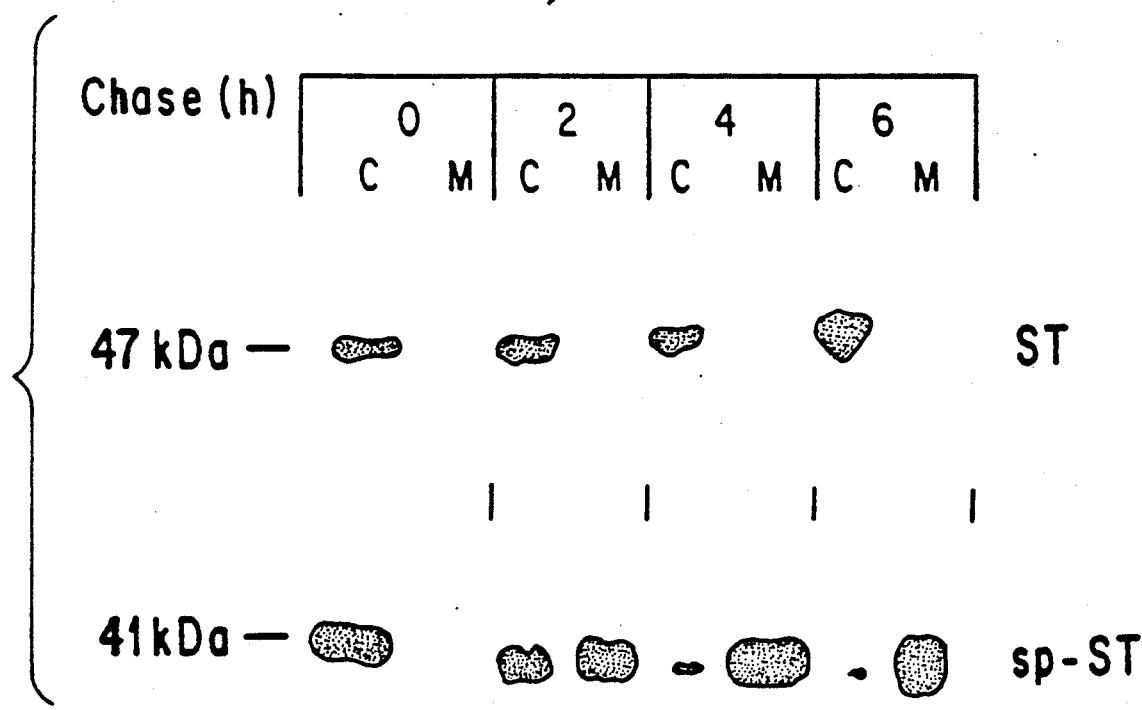
FIG. 4 depicts test results showing secretion of the soluble sialyltransferase (sp-ST) by Chinese hamster ovary (CHO) cells.

The wild type (ST) sialyltransferase (47 kDa) has previously been demonstrated to be catalytically active when expressed in stably transfected CHO cells which are lacking an endogenous β-galactoside α2,6 sialyltransferase (26). The above described pulse-chase analysis and immunoprecipitation of sialyltransferase protein from cell lysates and media of CHO cells revealed that the wild type sialyltransferase remains cell associated for up to 6 hours of chase and is not detected in the media for up to 24 hours (see FIG. 4). In contrast to the wild type sialyltransferase, the sp-ST fusion protein construct is rapidly secreted from CHO cells. At least 50% of the total sp-ST protein is secreted within 2 hours of chase, following a 1 hour labeling period (see FIG. 4). Moreover, the apparent molecular weight of the sp-ST (41 kDa) is consistent with the cleavage of the 2.5 kDa gamma interferon signal peptide.

Endo-β-N acetylglucosaminidase H (Endo H) preferentially cleaves high mannose N-linked oligosaccharides and can be used to trace the movement of secretory proteins from the ER to medial-Golgi apparatus where processing reactions convert the sugar chains to Endo H resistant forms (2,35). Endo H sensitivity of the N-linked oligosaccharides of both the intracellular and secreted forms of the sp-ST, which contains two N-linked sugar chains, is shown in FIG. 5. The intracellular form of the sp-ST protein (41 kDa) is predominantly Endo H sensitive and yields a single band with an apparent molecular weight of 35 kDa consistent with the cleavage of both N-linked carbohydrate groups. In contrast, the secreted sp-ST fusion protein is largely resistant to Endo H yielding 38 kDa and 41 kDa bands, indicating the resistance of one or both N-linked carbohydrate groups to enzyme digestion, respectively. Because these resistant forms of the sp-ST do not accumulate intracellularly, the results suggest that the rate limiting step in the secretion of the sp-ST is in the protein's migration from ER to the Golgi apparatus. Once the sp-ST oligosaccharides are processed in the Golgi apparatus, the sp-ST protein is rapidly secreted.

Figure 6:
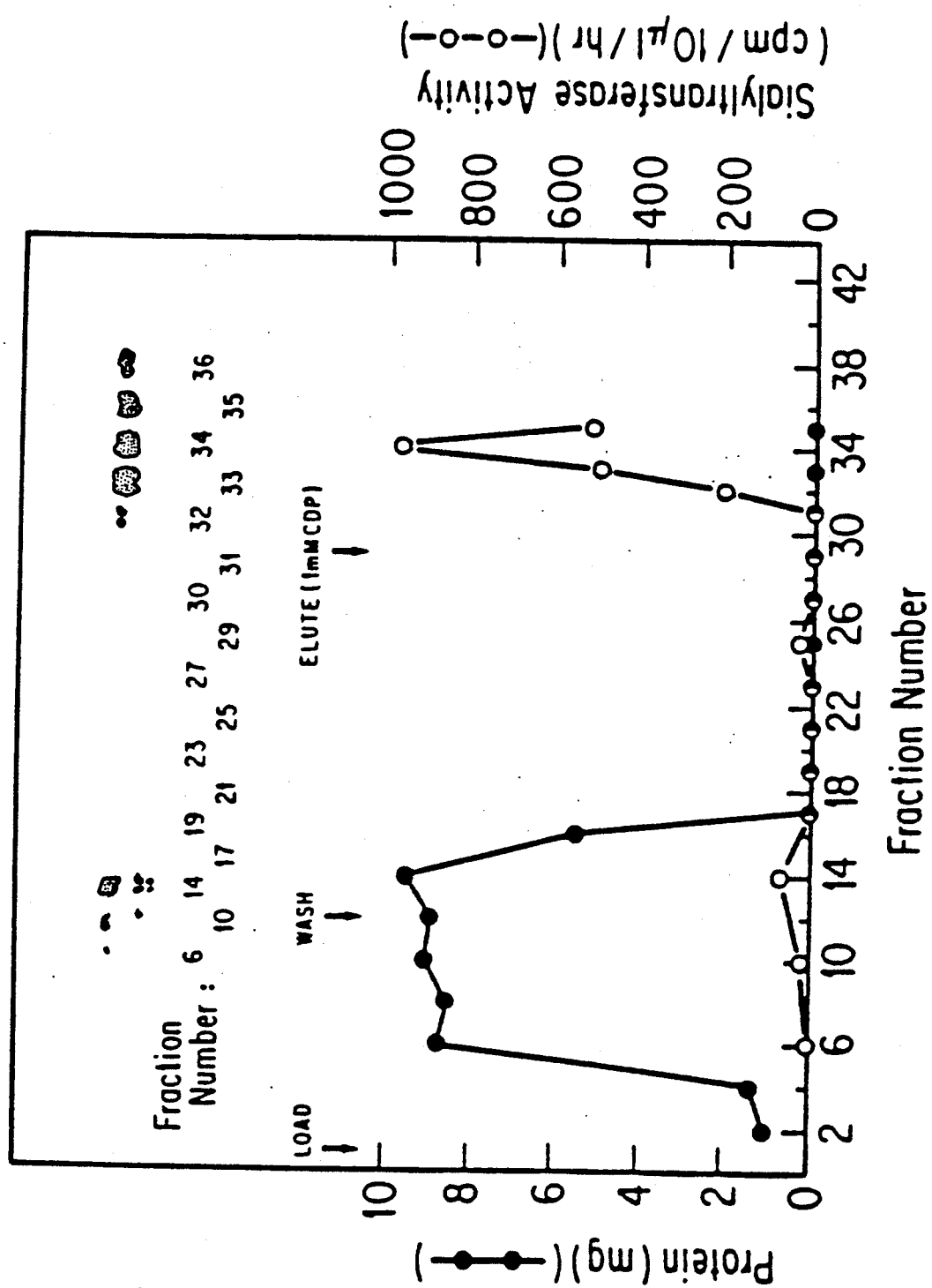
FIG. 6 depicts test results showing that the soluble sp-ST retains sialyltransferase activity.
Figure 7:
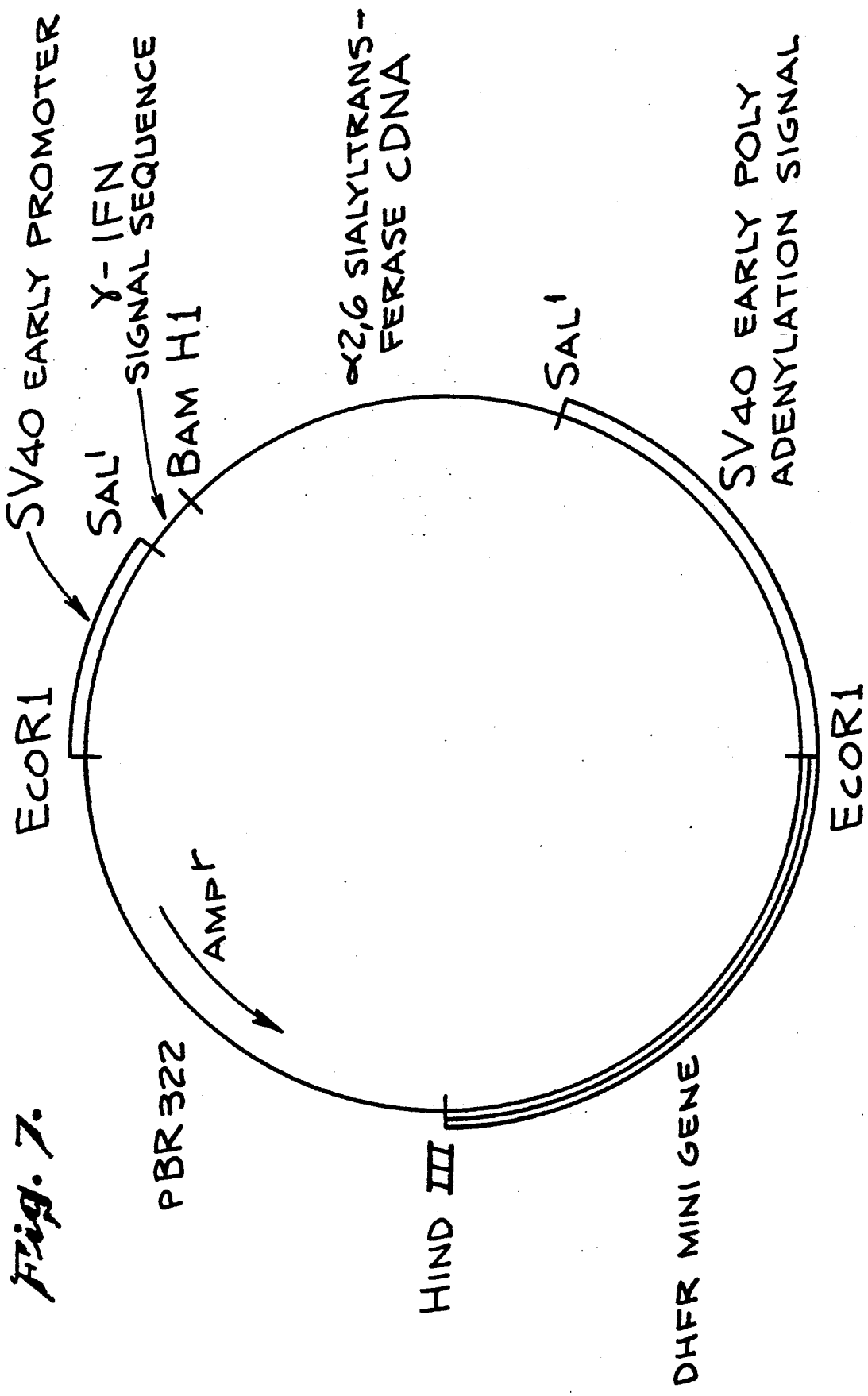
FIG. 7 is a diagram showing the exemplary vector construction used to transfect CHO with the gene expressing the soluble sp-ST protein.

As with the wild type sialyltransferase, the CHO cells expressing the sp-ST synthesize the product of the enzyme detected by the FITC-SNA lectin which shows that the soluble sialyltransferase exhibits catalytic activity during transit through the cell. Moreover, direct enzyme assays detected sialyltransferase activity in the media of CHO cells secreting the sp-ST protein, but not in the media of parental CHO cells or CHO cells expressing the wild type sialyltransferase. This shows that the soluble enzyme is active once secreted from the cells. The ability of sp-ST to bind to the affinity absorbent CDP-hexanolamine-agarose used in the purification of the rat liver sialyltransferase was tested (33). As demonstrated in FIG. 6, sialyltransferase activity in the CHO cell media is bound to the column and elutes with the free ligand CDP. Moreover, the bulk of the immunoprecipitable $^{35}$S-labeled sp-ST accumulated throughout a 24 hour chase period is also bound to the column and is specifically eluted with CDP. Taken together, these results demonstrate that the secreted enzyme is catalytically active and is stable in the media.

Figure 2:
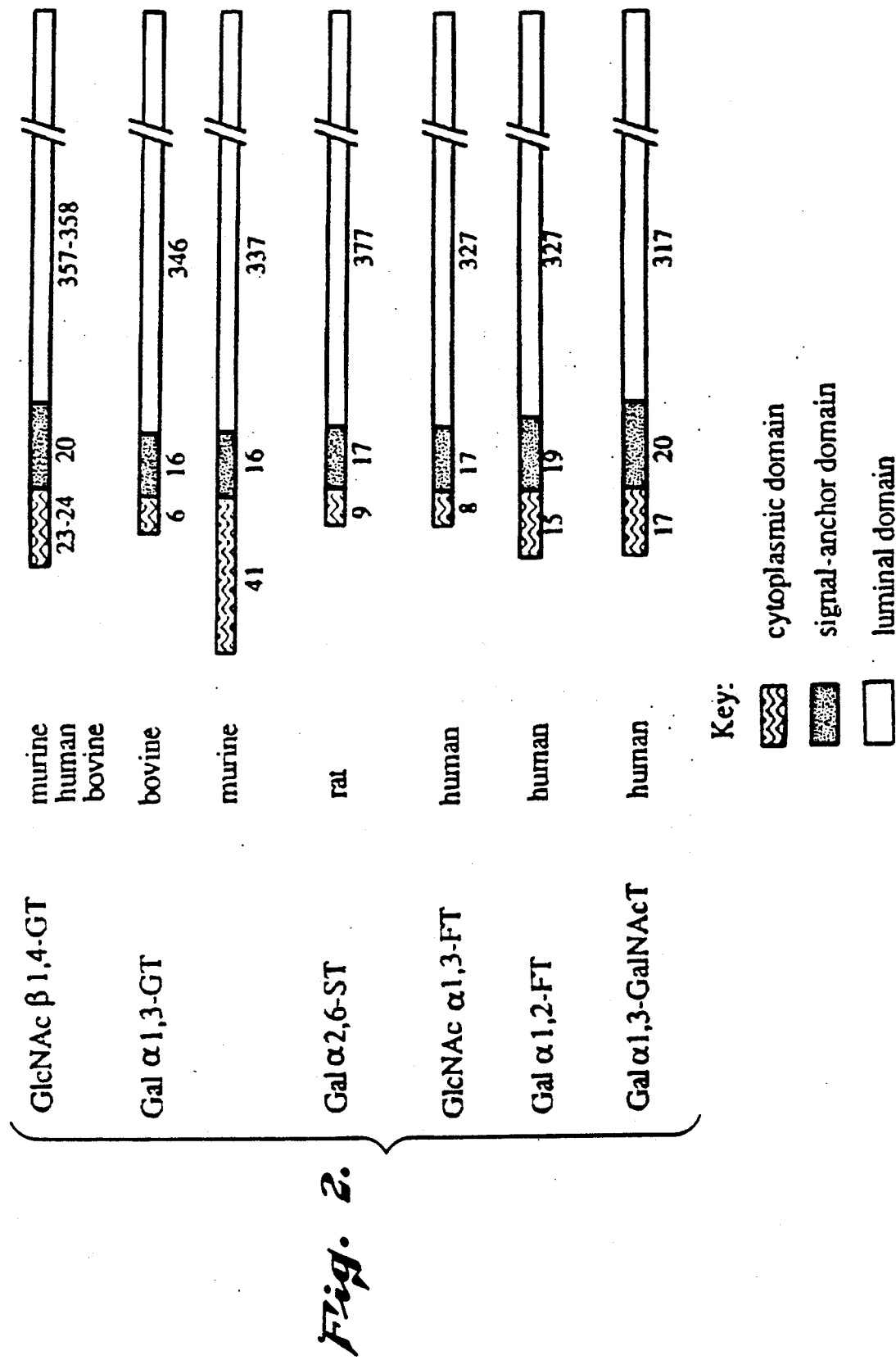
FIG. 2 compares the essential features of cloned cDNA's to other Golgi apparatus glycosyltransferases, all of which contain $NH_2$-terminal hydrophobic membrane domains, predicting each to have the same topology as the sialyltransferase (44).

The same principles illustrated in the above example can be extended to the production of any Golgi apparatus glycosyltransferase or other processing enzyme (glycosidase, sulfotransferase, acetyltransferase etc.) as a secretory protein providing that the enzyme has an NH$_2$-terminal signal-anchor sequence and has the Golgi retention signal in the NH$_2$-terminal peptide sequence including the cytoplasmic tail, membrane anchor and stem regions which are not required for catalytic activity. All Golgi apparatus glycosyltransferases whose cDNAs have been cloned meet this criterion (FIG. 2 and Table I). In addition, a Golgi glycosidase, mannosidase II, has also been shown to have a similar domain structure to the exemplary sialyltransferase illustrated in FIG. 1 (48).

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiment illustrated herein, but is only limited by the following claims.

BIBLIOGRAPHY

1. Pfeffer, S. and Rothman, J. E. (1987) Annu. Rev. Biochem. 56, 829-852.
2. Wieland, F. T., Gleason, M. L., Serafini, T. A., and Rothman, J. E. (1987) Cell 50, 289-300.
3. Klausner, R. D. (1989) Cell 57, 703-706.
4. von Figura, K. and Hasilik, A. (1986) Annu. Rev. Biochem. 55, 167-193.
5. Kornfeld, S. (1986) J. Clin. Invest. 77, 1-6.
6. Munro, S. and Pelham, H. R. B. (1987) Cell 48, 899-907.
7. Pelham, H. R. B. (1988) EMBO J. 7, 913-918.
8. Paabo, S., Bhat, B. M., Wold, W. S. M., and Peterson, P. A. (1987) Cell 50, 311-317.

9. Poruchynsky, M. S. and Atkinson, P. H. (1988) J. Cell Biol. 107, 1697-1706.
10. Stirzaker, S. C. and Both, G. W. (1989) Cell 56, 741-747.
11. Machamer, C. E. and Rose, J. K. (1987) J. Cell Biol. 105, 1205-1214.
12. Fleischer, B. (1981) J. Biol. Chem. 89, 246-255.
13. Kornfeld, R. and Kornfeld, S. (1985) Annu. Rev. Biochem. 54, 631-664.
14. Roth, J., Taatjes, D. J., Lucoq, J. M., Weinstein, J., and Paulson, J. C. (1985) Cell 43, 287-295.
15. Roth, J., Taatjes, D. J., Weinstein, J., Paulson, J. C., Greenwell, P., and Watkins, W. M. (1986) J. Biol. Chem. 261, 14307-14312.
16. Taatjes, D. J., Roth, J., Weinstein, J., and Paulson, J. C. (1988) J. Biol. Chem. 263, 6302-6309.
17. Weinstein, J., Lee, E. U., McEntee, K., Lai, P. -H., and Paulson, J. C. (1987) J. Biol. Chem. 263, 17735-17743.
18. Paulson, J. C., Beranek, W. E., and Hill, R. L. (1977) J. Biol. Chem. 252, 2356-2362.
19. Hudgin, R. L. and Schachter, H. (1971) Can. J. Biochem. 49, 829-837.
20. Kaplan, H. A., Woloski, B. M. R. N. J., Hellman, M., and Jamieson, J. C. (1985) J. Biol. Chem. 258, 11505-11509.
21. Lammers, G. and Jamieson, J. C. (1988) Biochem. J. 256, 623-631.
22. Paulson, J. C. Weinstein, J., Ujita, E. L., Riggs, K. J., and Lai, P. -H. (1987) Biochem. Soc. Trans. 15, 618-620.
23. Ellis, L., Clauser, E., Morgan, D. O., Edery, M., Roth, R. A., and Rutter, W. A. (1986) Cell 45, 721-732.
24. Zoller, J. J. and Smith, M. (1983) Meth. Enzymol. 100, 468-500.
25. Gasser, C. S., Simonsen, C. C., Schilling, J. W., and Schimke, R. T. (1982) Proc. Natl. Acad. Sci. U.S.A. 79, 6522-6526.
26. Lee, E. U., Roth, J., and Paulson, J. C. (1989) J. Biol. Chem., in press.
27. Graham, F. L. and van der Eb, A. J. (1973) Virology, 52, 456-467.
28. Wigler, M., Pellicer, A., Silverstein, S., and Axel, R. (1978) Cell 41, 725-731.
29. Lewis, W. H., Srinivasan, P. R., Siokoc, N., and Siminovitch, L. (1980) Somatic Cell Genetics 6, 333-347.
30. Laemmli, U. K. (1970) Nature 227, 680-685.
31. Bonner, W. M. and Lasky, R. A. (1974) Eur. J. Biochem. 46, 83-88.
32. Dahms, N. M., Lobel, P., Breitmeyer, J., Chirgwin, J. M., and Kornfeld, S. (1987) Cell 50, 181-192.
33. Weinstein, J., de Souza-e-Silva, U., and Paulson, J. C. (1982) J. Biol. Chem. 257, 13835-13844.
34. Gray, P. and Goeddel, D. V. (1982) Nature 298, 859-863.
35. Maley, F. and Trimble, R. B. (1981) J. Biol. Chem. 256, 1088-1090.
36. Roth, J. and Berger, E. G. (1982) J. Cell Biol. 93, 223-229.
37. Shaper, N. L., Hollis, G. F., Douglas, J. G., Kirsch, I. R., and Shaper, J. H. (1988) J. Biol. Chem. 263, 10420-10428.
38. Nakazawa, K., Ando, T., Kimura, T., and Narimatsu, H. (1988) J. Biochem. (Tokyo) 104, 165-168.
39. Masri, K. A., Appert, H. E., and Fukuda, M. N. (1988) Biochem. Biophys. Res. Comm. 157, 657-663.
40. Berger, E. G. and Hesford, F. J. (1985) Proc. Natl. Acad. Sci. U.S.A. 82, 4736-4739.
41. Duncan, J. R. and Kornfeld, S. (1988) J. Cell Biol. 106, 617-628.
42. Beyer, T. A., Sadler, J. E., Rearick, J. I., Paulson, J. C., and Hill, R. L. (1981) Adv. Enzymol. 52, 23-175.
43. Toone, E. J., Simon, E. S., Bednarski, M. D., and Whitesides, G. M. (1989) Tetrahed. Rep., in press.
44. Colley, K. J., Lee, E. U., Adler, B., Browne, J. K. and Paulson, J. C. (1989) J. Biol. Chem. 264, in press.
45. Ash, J. F., Fineman, R. M., Kalka, T., Morgan, M. and Wire, B. (1984) J. Cell Biol. 99, 971-983.
46. Smith, G. E., Summers, M. D. and Fraser, M. J. (1983) Mol. Cell Biol. 3, 2156-2165.
47. Hsueh, E. C., Holland, E. C., Carrera, G. M., and Drickamer, K. (1986) J. Biol. Chem. 261, 4940-4947.
48. Moreman, K. W. (1989) Proc. Nat. Acad. Sci. U.S.A. 86 5276-5280.

What is claimed is:

1. A method for producing a soluble glycosyltransferase which is secreted by a cell having Golgi apparatus as part of the secretory pathway of said cell, wherein the naturally occurring glycosyltransferase includes a membrane anchor and a retention signal located in an $NH_2$-terminal region not required for catalytic activity, said method comprising the steps of:
introducing into said cell at least one gene which is capable of expressing a soluble and secretable glycosyltransferase wherein said anchor domain and a sufficient portion of said $NH_2$-terminal region is replaced with a cleavable signal sequence so that said glycosyltransferase lacks said membrane anchor and said retention signal;
expressing said soluble and secretable glycosyltransferase in said cell wherein said cell secretes said soluble enzyme via said secretory pathway which includes said Golgi apparatus; and
recovering the soluble glycosyltransferase secreted by said cell.

2. A method for producing a secretable glycosyltransferase according to claim 1 wherein said glycosyltransferase is selected from the group consisting of N-acetylglucosaminyltransferases, N-acetylgalactosaminyltransferases, sialyltransferases, fucosyltransferases, galactosyltransferases, mannosyltransferases, sulfotransferases, accetyltransferases and mannosidases.

3. A method for producing secretable glycosyltransferase according to claim 2 wherein said glycosyltransferase is a sialyltransferase.

4. A method for producing a secretable glycosyltransferase according to claim 3 wherein said sialyltransferase is β-galactoside α2,6-sialyltransferase.

5. A method for producing a secretable glycosyltransferase according to claim 1 wherein the cell into which said gene is introduced is selected from the group consisting of Chinese hamster ovary cells, mouse L cells, mouse A9 cells, baby hamster kidney cells, C127 cells, PC8 cells and insect cells.

6. A method for producing a secretable glycosyltransferase according to claim 2 wherein the cell into which said gene is introduced is selected from the group consisting of Chinese hamster ovary cells, mouse L cells, mouse A9 cells, baby hamster kidney cells, C127 cells, PC8 cells and insect cells.

7. A method for producing a secretable glycosyltransferase according to claim 3 wherein the cell into which said gene is introduced is selected from the group consisting of Chinese hamster ovary cells, mouse L cells, mouse A9 cells, baby hamster kidney cells, C127 cells, PC8 cells and insect cells.

8. A method for producing a secretable glycosyltransferase according to claim 4 wherein the cell into which said gene is introduced is selected from the group consisting of Chinese hamster ovary cells, mouse L cells, mouse A9 cells, baby hamster kidney cells, C127 cells, PC8 cells and insect cells.

9. A method for producing a secretable enzyme according to claim 1 wherein said gene is introduced into said cell by transfection with a vector comprising DNA which codes for said secretable glycosyltransferase.

10. A method for producing a secretable enzyme according to claim 9 wherein said vector is selected from the group consisting of pECE, pMSG, pAV00-9/A+, pMT010/A+, pMAMucc-S, bacculovirus and pDSVE.

11. A method for producing a secretable enzyme according to claim 10 wherein said vector is pDSVE.

12. In a method for producing glycosyltransferase wherein said glycosyltransferase is produced within a cell having Golgi apparatus as part of the secretory pathway of said cell and wherein said glycosyltransferase remains within said cell, said glycosyltransferase including a membrane anchor and a retention signal located in an NH$_2$-terminal region not required for catalytic activity region which causes said glycosyltransferase to be retained within said cell and an enzymatic domain which provides said glycosyltransferase with enzymatic activity, the improvement comprising:
   introducing at least one gene into said cell which is capable of expressing a glycosyltransferase in which said membrane anchor and a sufficient portion of said NH$_2$-terminal region is replaced with a cleavable signal sequence so that said glycosyltransferase lacks said membrane anchor and said retention signal whereby a soluble glycosyltransferase is produced which is secreted by the cell via said secretory pathway which includes said Golgi apparatus;
   expressing said soluble glycosyltransferase in said cell which is secreted by said cell; and
   recovering the soluble glycosyltransferase secreted by said cell.

13. The improved method for producing glycosyltransferase according to claim 12 wherein said glycosyltransferase is selected from the group consisting of N-acetylglucosaminyltransferases, N-acetylgalactosaminyltransferases, sialyltransferases, fucosyltransferases, galactosyltransferases, mannosyltransferases, sulfotransferases, accetyltransferases and mannosidases.

14. The improved method according to claim 12 wherein said gene expresses a glycosyltransferase having a γ-cleavable signal peptide substituted for the membrane anchor and retention signal, said cleavable signal peptide being selected from the group consisting of γ-interferon signal peptide, insulin signal peptide and TPA signal peptide.

15. The improved method according to claim 14 wherein said glycosyltransferase is a sialyltransferase.

16. The improved method according to claim 15 wherein said sialyltransferase is β-galactoside α2,6-sialyltransferase.

17. A composition of matter comprising cells which have Golgi apparatus as part of the secretory pathway of said cell and wherein said cells include at least one recombinant gene which encodes a soluble and secretable glycosyltransferase in which the anchor domain and a sufficient portion of the NH$_2$-terminal region of said glycosyltransferase is replaced with a cleavable signal sequence so that said glycosyltransferase lacks the membrane anchor and the retention signal, whereby said glycosyltransferase is secreted by the cell via said Golgi apparatus and said secretory pathway.

18. A composition of matter according to claim 17 wherein said gene encodes a soluble glycosyltransferase selected from the group sialyltransferases, fucosyltransferases, galactosyltransferases, mannosyltransferases, sulfotransferases, accetyltransferases and mannosidases.

19. A composition of matter according to claim 17 wherein said cells are selected from the group consisting of Chinese hamster ovary cells, mouse L cells, mouse A9 cells, baby hamster kidney cells, C127 cells, PC8 cells and insect cells.

20. A composition of matter according to claim 18 wherein said cells are selected from the group consisting of Chinese hamster ovary cells, mouse L cells, mouse A9 cells, baby hamster kidney cells, C127 cells, PC8 cells and insect cells.

21. A composition of matter according to claim 17 wherein said gene is introduced into said cell by transfection with a vector comprising DNA which codes for said glycosyltransferase.

22. A vector for use in expressing a soluble sialyltransferase in a host cell, said vector comprising DNA having a nucleotide sequence which codes for a sialyltransferase which lacks the membrane anchor and retention signal of said sialyltransferase.

23. A vector according to claim 22 wherein said DNA is inserted in a vector selected from the group consisting of pECE, pMSG, pAV009/A+, pMT010/A+, pMAMucc-S, bacculovirus and pDSVE.

* * * * *